United States Patent
Watanabe et al.

(10) Patent No.: US 7,308,913 B2
(45) Date of Patent: Dec. 18, 2007

(54) LIQUID FILLING METHOD, LIQUID FILLING APPARATUS, AND DISCHARGE APPARATUS

(75) Inventors: Nobuko Watanabe, Kanazawa (JP); Takeo Kawase, Suwa (JP); Hirotsuna Miura, Fujimi (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 11/398,067

(22) Filed: Apr. 5, 2006

(65) Prior Publication Data
US 2006/0180239 A1 Aug. 17, 2006

Related U.S. Application Data

(62) Division of application No. 10/679,949, filed on Oct. 6, 2003, now Pat. No. 7,051,773.

(30) Foreign Application Priority Data

Oct. 15, 2002 (JP) ............................ 2002-300370
Sep. 2, 2003 (JP) ............................ 2003-310452

(51) Int. Cl.
*B65B 31/00* (2006.01)
(52) U.S. Cl. ......................................... 141/7; 141/130
(58) Field of Classification Search ............ 141/4, 141/7, 24–26, 65, 67, 130, 234–242; 422/99, 422/100; 73/863.32, 864.13
See application file for complete search history.

(56) References Cited

U.S. PATENT DOCUMENTS

| | | | |
|---|---|---|---|
| 4,810,471 A | 3/1989 | Wachob et al. | 422/103 |
| 5,343,909 A * | 9/1994 | Goodman | 141/242 |
| 6,006,800 A | 12/1999 | Nakano | 141/130 |
| 6,221,653 B1 | 4/2001 | Caren et al. | 435/287.2 |
| 6,492,162 B1 | 12/2002 | Sakurai et al. | 435/285.1 |
| 6,509,193 B1 | 1/2003 | Tajima | 436/49 |
| 6,764,648 B1 | 7/2004 | Roach et al. | 422/63 |

FOREIGN PATENT DOCUMENTS

JP  2001-324505  11/2001

* cited by examiner

*Primary Examiner*—Timothy L. Maust
(74) *Attorney, Agent, or Firm*—Harness, Dickey & Pierce, P.L.C.

(57) ABSTRACT

A liquid filling apparatus includes a discharge head having a cavity for storing liquid, a nozzle communicated with the cavity, and a discharge device for discharging liquid stored in the cavity through the nozzle. In addition, the apparatus includes a liquid supply section which supplies the liquid to the nozzle of the discharge head by contacting the liquid with the nozzle, and a suction device connected to a cavity side of the discharge head, which draws liquid supplied from the liquid supply section to inside the cavity, by suction from the nozzle via the cavity.

1 Claim, 9 Drawing Sheets

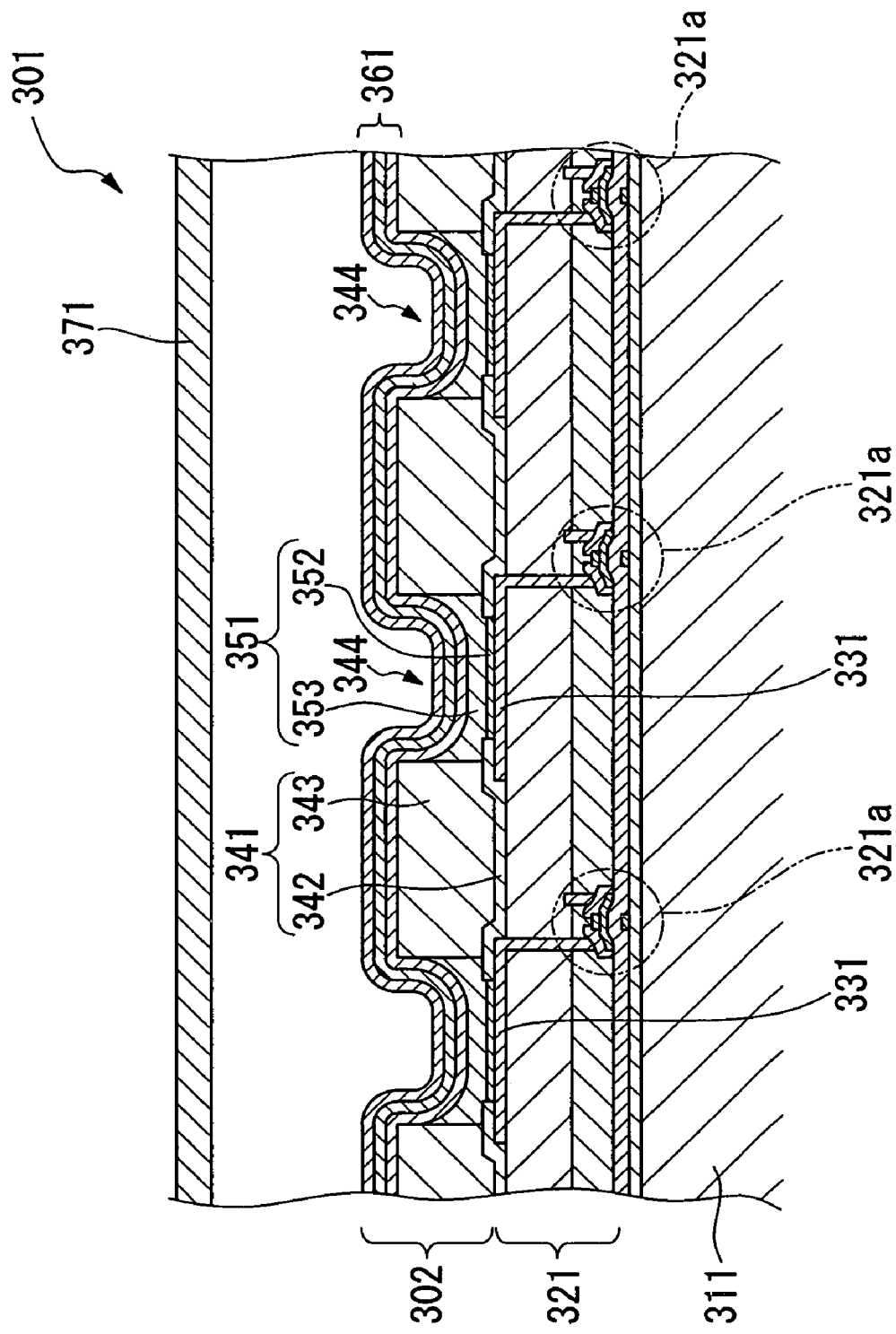

LIQUID FILLING METHOD, LIQUID FILLING APPARATUS, AND DISCHARGE APPARATUS

This application is a divisional patent application of U.S. Ser. No. 10/679,949 filed Oct. 6, 2003 now U.S. Pat. No. 7,051,773 which claims priority to JP 2002-300370 filed Oct. 15, 2002 and JP 2003-310452 filed Sep. 2, 2003, all of which are hereby incorporated by reference.

BACKGROUND OF THE INVENTION

1. Field of the Invention

The present invention relates to a method and apparatus for filling liquid into a desired position. In particular, it relates to a liquid filling method to fill expensive reagents, scarce specimens, or the like, a liquid filling apparatus, and furthermore a discharge apparatus incorporating the filling apparatus.

2. Description of Related Art

There has been remarkable progress in methods of analyzing gene structures in recent years, and large numbers of gene structures have been identified, including the human gene and others. For such analysis of gene structures, a method is used in which thousands to tens of thousands or more different DNA fragments are placed and aligned on a substrate such as a microscope slide glass or the like in droplets, forming test objects, and they are observed by microscope or the like.

However, in the case where thousands or more objects are produced, such as when producing test objects, it is very inefficient to carry out this operation totally manually. Therefore, automation is required.

A method of automation that can be used is a filling apparatus that discharges liquid such as a reagent or the like, and fills it into test objects. An example of a filling apparatus for discharging liquid is a droplet discharge apparatus, called an inkjet apparatus, used in printers and the like as described in Japanese Unexamined Patent Application, First Publication No. 2001-324505.

Typically, such a droplet discharge apparatus is provided with a liquid cavity tank behind a discharge head, and supplies liquid from the liquid cavity tank to the discharge head, and discharges droplets (liquid) from the nozzles of the discharge head.

However, for producing test objects or the like using DNA fragments as mentioned previously, specimens to be used such as DNA or the like are scarce, and many reagents to be used are expensive. Therefore, it is difficult to collect a large quantity of liquid as a reagent in the liquid cavity tank, and supply it to the discharge head to discharge droplets (liquid) from the nozzles. This is because in the case where liquid is discharged from the discharge head, evidently the liquid fills the discharge head, and in order to discharge it accurately, it is necessary to prevent air (air bubbles) from entering and remaining in the discharge path, or to remove residual air bubbles.

However, as mentioned above, in the case where a liquid cavity tank is provided, liquid must fill the path from the liquid cavity tank to the discharge head, and also a test discharge of the liquid must be performed in order to remove air (air bubbles) mixed therein. Consequently, a large amount of liquid (reagent) is required, and a lot is wasted, which is a cost disadvantage, so basically this method cannot be used for scarce liquids.

The present invention takes the above situations into consideration, with an object of providing a liquid filling method that can fill expensive reagents, scarce specimens, or the like, easily and reliably, a liquid filling apparatus, and a discharge apparatus incorporating the filling apparatus.

SUMMARY OF THE INVENTION

The first aspect of the present invention is a liquid filling method for filling a liquid into a desired location using a discharge head having a cavity for storing a liquid, a nozzle communicated with the cavity, and a discharge device for discharging liquid stored in the cavity through the nozzle, the liquid filling method having the steps of contacting the nozzle of the discharge head with a liquid prepared in advance, drawing the liquid through the nozzle, and storing the drawn liquid in the cavity, and discharging liquid stored in the cavity using the discharge device.

In the liquid filling method, since liquid is drawn through the nozzle and stored in the cavity, and afterwards the stored liquid is discharged through the nozzle by the discharge device, it is possible to draw into the discharge head only the minimum amount of liquid that can be discharged from the cavity through the nozzle by the discharge device. Accordingly, even in the case of expensive or scarce liquid, a small amount of liquid can be discharged without waste.

Furthermore, it is preferable that the liquid and the nozzle of the discharge head be contacted by dipping the discharge head into the liquid.

As a result, the minimum required amount of liquid can be prepared, and waste of liquid prevented, reliably.

Furthermore, the liquid and the nozzle of the discharge head may be contacted by facing the surface in which the nozzle of the discharge head is formed upwardly, and arranging the liquid so as to cover the entire nozzle.

In this case also, the minimum required amount of liquid can be prepared, and waste of liquid prevented, reliably.

Moreover, the liquid and the nozzle of the discharge head may be contacted by facing the surface in which the nozzle of the discharge head is formed downwardly, and supplying the liquid to the nozzle by a dispenser from below this surface.

This enables the process to be performed with the surface in which the nozzle is formed facing downwardly, so that it is possible to discharge immediately after the liquid is drawn up.

The second aspect of the present invention is a liquid filling apparatus having a discharge head having a cavity for storing liquid, a nozzle communicated with the cavity, and a discharge device for discharging liquid stored in the cavity through the nozzle, a liquid supply section which supplies the liquid to the nozzle of the discharge head by contacting the liquid with the nozzle, and a suction device connected to a cavity side of the discharge head, which draws liquid supplied from the liquid supply section to inside the cavity, by suction from the nozzle via the cavity.

According to this liquid filling apparatus, by providing the liquid supply section and the suction device, then as mentioned above, liquid supplied from the liquid supply section by the suction device can be drawn through the nozzle and stored in the cavity, after which the stored liquid can be discharged through the nozzle by the discharge device. Therefore it is possible to draw into the discharge head only the minimum amount of liquid that can be discharged from the cavity through the nozzle by the discharge device. Accordingly, even in the case of expensive liquid or scarce liquid, a small amount of liquid can be discharged without waste.

It is preferable that the discharge head have a reservoir which stores liquid on a side of the cavity opposite the nozzle, and an opening and closing valve is provided between the cavity and the reservoir for opening and closing a channel therebetween.

By so doing, when liquid drawn into and stored in the cavity by the suction device is discharged through the nozzle by the discharge device, the channel between the reservoir and the cavity is closed by the opening and closing valve so that the liquid is discharged from the nozzle side reliably without flowing back to the reservoir side.

Furthermore, the discharge head may have a reservoir which stores liquid on a side of the cavity opposite the nozzle, and the reservoir may have a pressurizing device for pressurizing the cavity.

By so doing, when liquid drawn into and stored in the cavity by the suction device is discharged through the nozzle by the discharge device, the cavity is pressurized by the pressurizing device so that the liquid is discharged from the nozzle side reliably without flowing back to the reservoir side.

The third aspect of the present invention is a discharge apparatus having the above-described liquid filling apparatus, and a moving mechanism for moving the discharge head of the liquid filling apparatus.

According to this discharge apparatus, since the discharge head of the filling apparatus can be moved, it is possible to discharge liquid from the discharge head to a desired position. Furthermore, it is possible to discharge liquid by the filling apparatus rapidly and efficiently.

BRIEF DESCRIPTION OF THE DRAWINGS

FIG. 10 is a sectional side elevation of an organic EL device.

DETAILED DESCRIPTION OF THE INVENTION

Hereunder is a detailed description of the present invention.

Figure 1A:
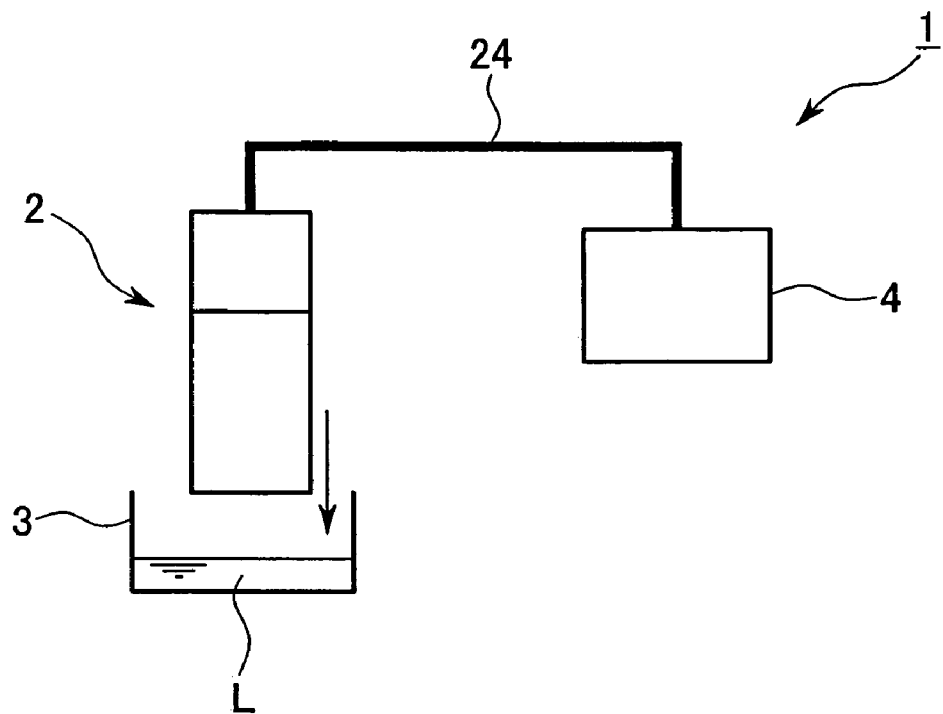
FIG. 1A and FIG. 1B are schematic block diagrams of a filling apparatus of the present invention.
Figure 1B:
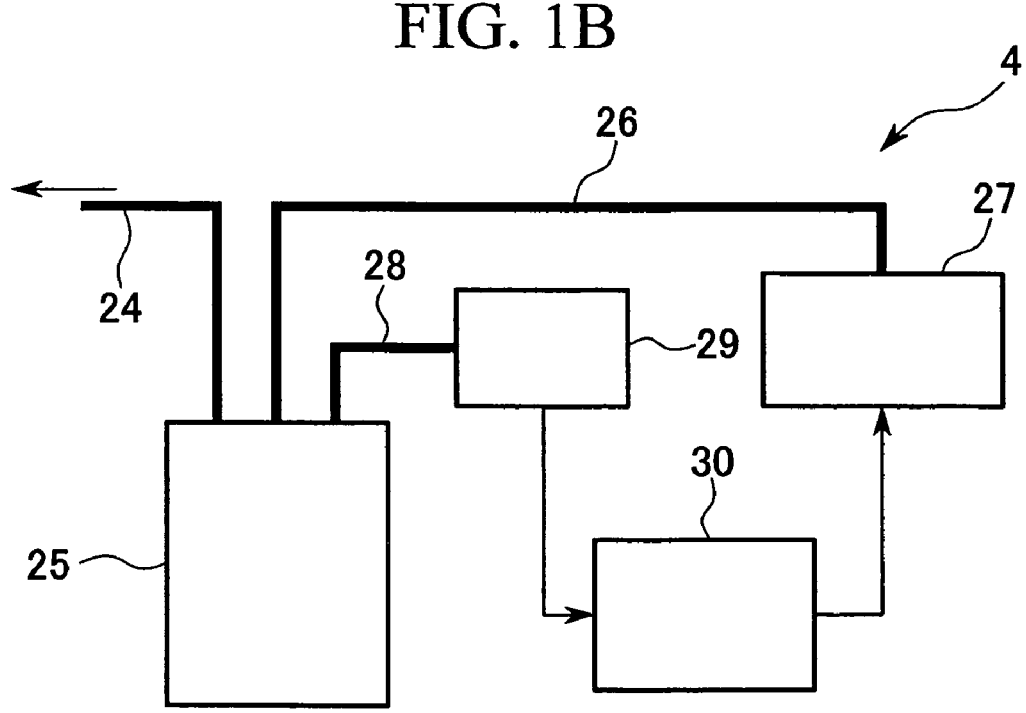

FIG. 1A and FIG. 1B are diagrams showing an example of a liquid filling apparatus of the present invention. Reference number 1 in FIG. 1A denotes the liquid filling apparatus (referred to hereunder as a filling apparatus).

The filling apparatus 1 includes a discharge head 2, a container 3 for storing liquid for discharge, and a pressure controller 4, which is provided with a suction device for drawing liquid into the discharge head 2.

Figure 2A:
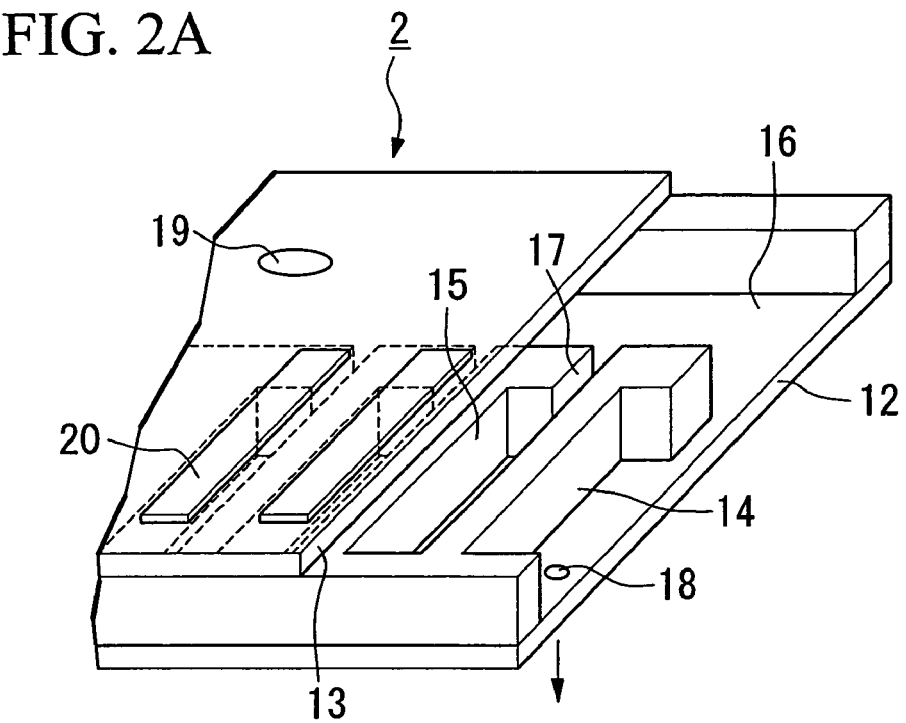
FIG. 2A and FIG. 2B are schematic block diagrams of a discharge head.

As shown in FIG. 2A, the discharge head 2 has a nozzle plate 12 made of stainless steel, and a diaphragm 13, with the two joined via partitions (cavity plates) 14. A plurality of cavities 15 and a reservoir 16 are formed by the partitions 14 between the nozzle plate 12 and the diaphragm 13, and the cavities 15 and the reservoir 16 are communicated via channels 17.

The cavities 15 and the reservoir 16 are filled with liquid, and the channels 17 therebetween function as supply ports for supplying liquid from the reservoir 16 to the cavities 15. Furthermore, a plurality of nozzle holes 18 for ejecting liquid from the cavities 15 is formed in rows along the length and width of the nozzle plate 12. Moreover, a hole 19 is formed in the diaphragm 13 to vent the reservoir 16. The above-described pressure controller 4 is connected to this hole 19 via a tube 24 (refer to FIG. 1A).

Figure 2B:
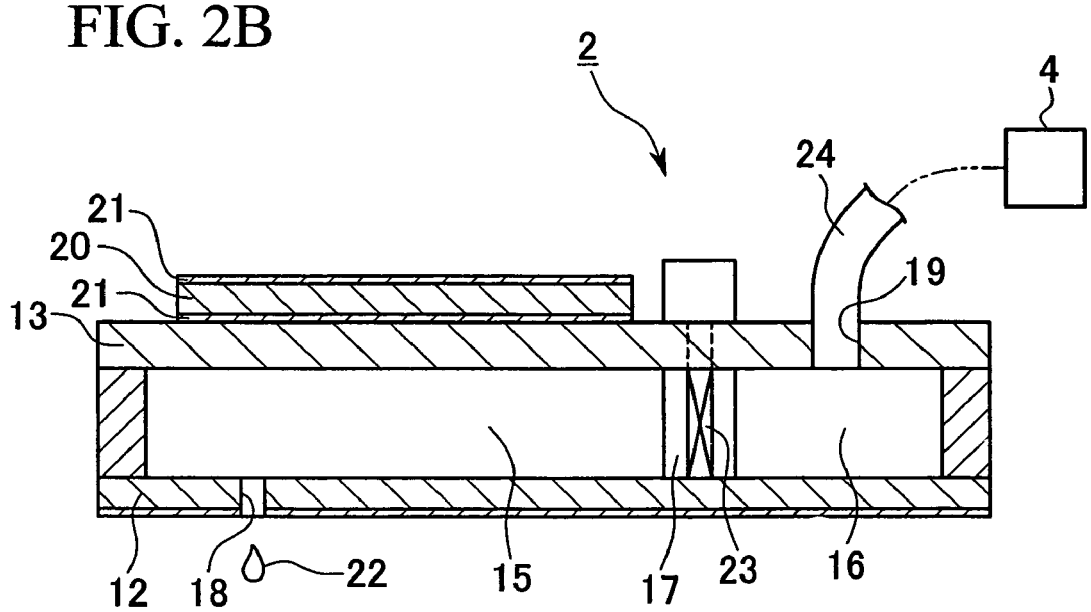

Furthermore, piezoelectric elements (piezo elements) 20 are attached on the surface opposite the surface facing toward the cavities 15 of the diaphragm 13 as shown in FIG. 2B. The construction is such that the piezoelectric elements 20 are sandwiched between pairs of electrodes 21 and 21, and flex outward when electricity is applied, and they function as discharge devices in the present invention.

The diaphragm 13 on which the piezoelectric elements 20 are fitted in such a construction flexes outward together with the piezoelectric elements 20, thus increasing the capacity of the cavities 15. The cavities 15 and the reservoir 16 are communicated, so in the case where the reservoir 16 is filled with liquid, an amount of liquid corresponding to the increase in volume flows from the reservoir 16 to the cavities 15 via the channels 17.

When the electricity flowing to the piezoelectric elements 20 is stopped, the piezoelectric elements 20 and the diaphragm 13 return to their original shapes. Therefore, the cavities 15 also return to their original capacities, so that the pressure of liquid inside the cavities 15 increases, and liquid droplets 22 are discharged from the nozzles 18.

Moreover, a solenoid valve (opening and closing valve) 23 is provided in each channel 17 for opening and closing the channel. Accordingly, when the solenoid valves 23 are closed, between the cavities 15 and the reservoir 16 is closed, which prevents liquid in the cavities 15 from flowing back to the reservoir 16. That is, as described later, in the case where only a small amount of liquid can be drawn up, the reservoir 16 may not be filled with liquid sufficiently. However, in the case where liquid is discharged from the nozzles 18 in such a state, by closing the channels 17 between the cavities 15 and the reservoir 16 by the solenoid valves 23, it is possible to discharge liquid from the nozzles 18 without flowing back to the reservoir 16.

Devices other than an electromechanical converter using the above-described piezoelectric elements (piezo elements) 20 may be used as the inkjet head discharge device. Examples of methods involve; a method using an electromechanical converter as an energy generator, a continuous method such as with an electrostatic control type or an oscillatory pressure type, an electrostatic suction method, and furthermore a method in which electromagnetic waves such as from a laser are radiated to generate heat, and liquid is discharged by the effects of this heat generation.

The container 3 is a liquid supply section in the present invention, inside of which liquid L is stored as shown in FIG. 1A. There is no particular limitation to this container 3, and any can be used provided it is of a shape and size into which the discharge head 2 can be placed and dipped into the stored liquid. For example, a beaker, a petri dish, a glass reagent bottle, or the like can be used. However, depending on the type of liquid used, the material must obviously be one that does not change the character of the liquid.

The pressure controller 4 is connected to the hole 19 of the discharge head 2 via the tube 24, and comprises a buffer tank 25 connected to the tube 24, a pressure generator 27 connected to the buffer tank 25 via a tube 26, a pressure sensor 29 connected to the buffer tank 25 via a tube 28, and a controller 30 for controlling the pressure generator 27.

The pressure generator 27 functions, in the present example, as a suction device and also as a pressurizing device, and it reduces or increases the pressure of the reservoir 16 by reducing or increasing the pressure of the buffer tank 25 connected via the tube 26. This pressure generator 27 may be one that has a pressure reducing pump (vacuum pump), a pressure increasing pump (air supply pump), with a mechanism for switching between pressure reducing and pressure increasing by a three way valve or the like, or may be a mechanism that uses a negative pressure source and a positive pressure source which use a device other than a pump, for example a header. Here, in the present example, both pressure reducing and pressure increasing can be performed. However, this pressure generator 27 does not necessarily perform both the pressure reducing and pressure increasing, and it is sufficient if it at least reduces the pressure sufficiently for suction via the discharge head 2 as described later.

The pressure sensor 29, which is formed from a conventionally known commercial pressure sensor, detects the pressure in the buffer tank 25, which is adjusted by the pressure generator 27, and sends a signal representing the voltage value obtained to the controller 30.

The controller 30, which controls the pressure generator 27 such that the buffer tank 25 attains a preset pressure, changes the level of pressure reduction of the pressure of the buffer tank 25 detected by the pressure sensor 29, or controls the pressure generator 27 to change the level of pressurization. Furthermore, this controller 30 can preset the pressure created inside the buffer tank 25 by the pressure generator 27, and can control the opening and closing of the solenoid valves 23 provided in the channels 17 of the discharge head 2.

By providing a moving mechanism that moves the discharge head 2, the filling apparatus 1 with such a construction can function as a discharge apparatus that can automatically discharge liquid to a desired position by the discharge head 2. Here, the moving mechanism has an X direction transfer device for moving the discharge head 2 of the filling apparatus 1 in the X direction, a Y direction transfer device for moving it in the Y direction, and a Z direction (height direction) transfer device. The arrangement is such that the transfer device can move the discharge head 2 accurately in the XY direction, being the horizontal direction, and the Z direction, being the height direction (vertical direction), by moving in 1 µm increments using a driving device such as a linear motor or the like.

Furthermore, the discharge head 2 can be attached to and removed from the moving mechanism. Hence operation is possible even in the case of discharging and placing drops of liquid manually.

Next is a description of an example of a liquid filling method of the present invention based on a method of using the filling apparatus 1 with the above-described construction.

Firstly, filling liquid L is prepared and placed in the container 3. Here, the present invention is suitable for use in filling especially expensive reagents, scarce specimens, or the like. Accordingly, the liquid L is only filled the minimum amount. Such liquid L is preferably degassed in advance.

Next, the discharge head 2 is placed in the container 3 in order to dip it into the liquid L. Then, the mechanism on the pressure reduction side of the pressure generator 27 of the pressure controller 4 is operated, and the pressure in the buffer tank 25 is reduced to a predetermined pressure. The solenoid valves 23 in the channels 17 of the discharge head are closed in advance of reducing the pressure. In this manner, when the solenoid valves 23 are closed, since the reservoir 16 in the discharge head 2 is connected to the buffer tank 25 via the tube 24, the pressure in this reservoir 16 is also reduced to the same pressure as the buffer tank 25.

Once the pressure of the buffer tank 25 has been reduced to the predetermined pressure in this manner, the solenoid valves 23 are opened by the controller 30. As a result, the channels 17 open, the cavities 15 are communicated with the reservoir 16, and the cavities 15 are communicated with the buffer tank 25 via the reservoir 16 and the tube 24. Accordingly, the pressure of the cavities 15 is reduced so that the cavities 15 draw the liquid L in the container 3 through the nozzles 18, and store it inside.

Once the liquid L has filled the cavities 15 in this manner, and the liquid L has flowed further into the reservoir 16, the controller 30 closes the solenoid valves 23. Alternatively, the mechanism (pressurizing device) on the pressurizing side of the pressure generator 27 is operated, and the pressure in the buffer tank 25 is pressurized to reach an atmospheric pressure or slightly higher. As a result, suction from the nozzles 18 stops.

Next, the discharge head 2 is pulled out of the container 3, and the liquid L adhering to the surface in which the nozzles 18 of the discharge head 2 are formed is wiped off as required.

Afterwards, by operating the piezoelectric elements 20 of the discharge head 2, droplets of the liquid are discharged at desired positions from the nozzles 18, and the liquid L fills the desired positions.

In addition, in the case where the discharge head 2 is provided with a moving mechanism to move it when operating the filling apparatus 1 as a discharge apparatus, the discharge head 2 is moved to a desired position by appropriate operation of the moving mechanism to discharge droplets (liquid L).

In such a liquid filling process, since the liquid L is drawn into the cavities 15 from the nozzles 18, after which the stored liquid L is discharged through the nozzles 18 by the piezoelectric elements 20, then for example it is possible to draw the minimum amount required for discharge, into the discharge head 2. Accordingly, even in the case of expensive liquid or scarce liquid, a small amount of liquid can be discharged without waste.

Furthermore, since the solenoid valves 23 are provided in the channels 17 between the cavities 15 and the reservoir 16, when the liquid L is discharged through the nozzles 18 by the piezoelectric elements 20, it is possible to discharge the liquid L from the nozzles 18 without flowing back to the reservoir 16 side, by closing the channels 17 using the solenoid valves 23. Accordingly, this is especially advantageous in the case where there is extremely little of liquid L, which cannot fill the reservoir 16 sufficiently.

On the other hand, in the case where there is comparatively ample liquid L, the liquid L also fills the reservoir 16. Furthermore, the liquid L also fills the tube 24, which is used as a liquid pool, after which the mechanism on the pressurizing side of the pressure generator 27 is operated as mentioned before to increase the pressure in the buffer tank to atmospheric pressure or slightly higher, which forms a back pressure. Then, by operating the piezoelectric elements 20 in this condition to discharge the liquid L through the nozzles 18, it is possible to discharge the liquid L from the nozzles 18 reliably without flowing back to the reservoir 16 side.

In the aforementioned example, the liquid L and the nozzles 18 of the discharge head 2 are contacted by dipping the discharge head 2 into the liquid L in the container 3. However, the present invention is not limited to this, and a range of contact methods can be used.

Figure 3A:
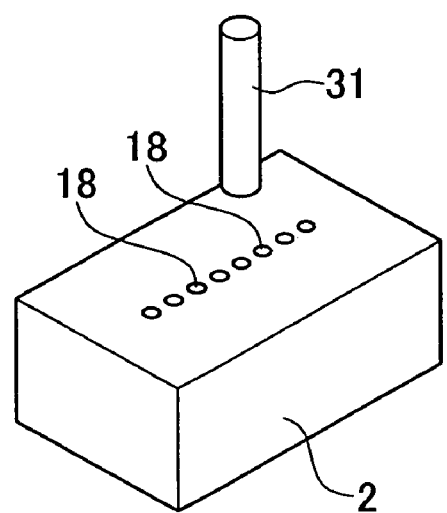
FIG. 3A to FIG. 3C are diagrams to explain another contact method.
Figure 3B:
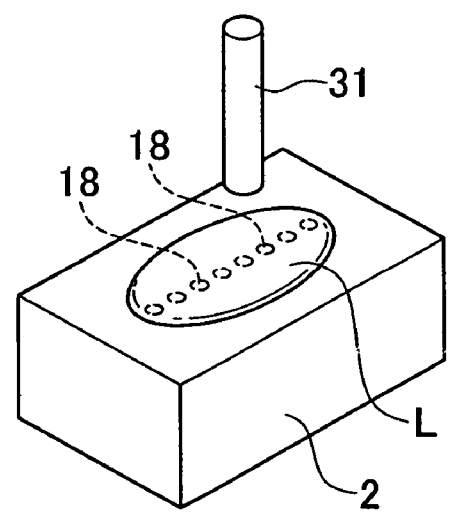
Figure 3C:
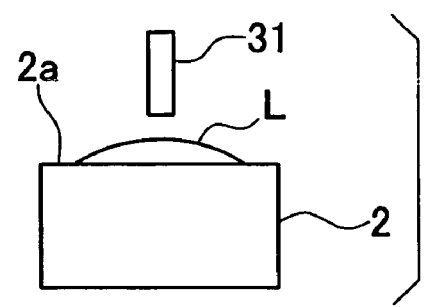

For example, as shown in FIG. 3A, the discharge head 2 may be placed upside down such that the surface in which the nozzles 18 are formed faces upwards. Then, in this condition, as shown in FIG. 3B and FIG. 3C, the liquid L is supplied to this surface in which the nozzles 18 are formed by a dispenser 31, for example, such that it covers all of the nozzles 18. Next, the liquid L lying on the surface in which the nozzles 18 are formed is drawn into the cavities 15 similarly to the above-described example. Then after the discharge head 2 is turned over again to direct the nozzles 18 downwards, the drawn up liquid L is discharged through the nozzles 18 similarly to the above-described example.

In this manner, the amount of liquid L placed is made to be the minimum required amount, and it is placed on the surface in which the nozzles 18 of the discharge head 2 are formed. Thus it is possible to prevent waste of liquid reliably.

When the liquid L placed on the surface in which the nozzles 18 are formed is drawn into the cavities 15, then in order to prevent air from being drawn in with the liquid L, the liquid L may be appropriately replenished to the surface in which the nozzles 18 are formed from the dispenser 31.

Figure 4A:
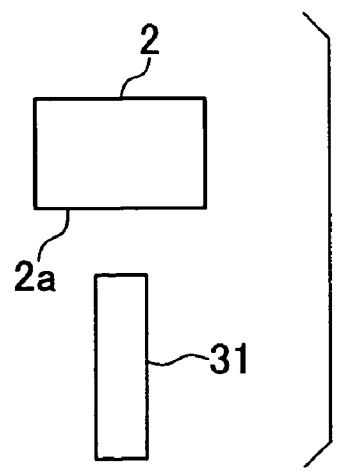
FIG. 4A to FIG. 4C are diagrams to explain another contact method.
Figure 4B:
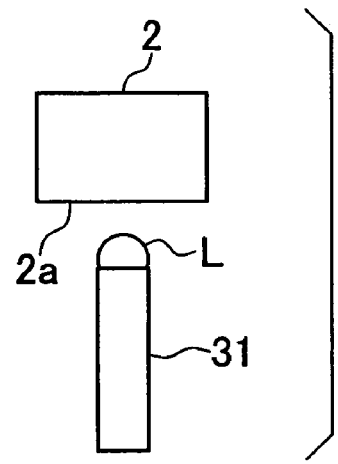
Figure 4C:
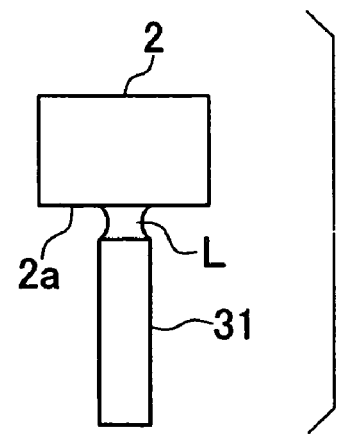

Furthermore, as shown in FIG. 4A to FIG. 4C, the arrangement may be such that with a surface 2a in which the nozzles 18 of the discharge head 2 are formed facing downwards, the liquid L is supplied to the nozzles 18 by the dispenser 31 from below this surface 2a. That is, as shown in FIG. 4B, the liquid L is pushed out as far as possible from the lip of the dispenser 31 while held by surface tension, and the dispenser 31 is moved in this state to close to the surface in which the nozzles 18 are formed. Then, the liquid L is suspended between the dispenser 31 and the surface 2a in which the nozzles 18 are formed as shown in FIG. 4C. Next, the suspended liquid L is drawn into the cavities 15 similarly to the above-described example. In this case, it is necessary to balance the supply of the liquid L from the dispenser 31 and the suction of the liquid L into the cavity 15, and ensure that the nozzles 18 are always covered with the liquid L, so that air does not flow into the cavities 15.

By so doing, compared with the case shown in FIG. 3, since the processing is performed with the surface 2a in which the nozzles of the discharge head 2 are formed facing downwards, it is possible to discharge immediately after the liquid L is drawn up.

In the above-described example, the filling liquid for discharge is an expensive reagent, a scarce specimen, or the like. However, it is not limited to these, and metal colloid, being a material for forming organic EL elements, or a range of materials such as micro lens material, color filter material, or liquid crystal material, can be used.

Hereunder is a description of an electro-optical device formed by discharging such material, and its system components.

Firstly, a liquid crystal display will be described as an example of an electro-optical device.

Figure 5:
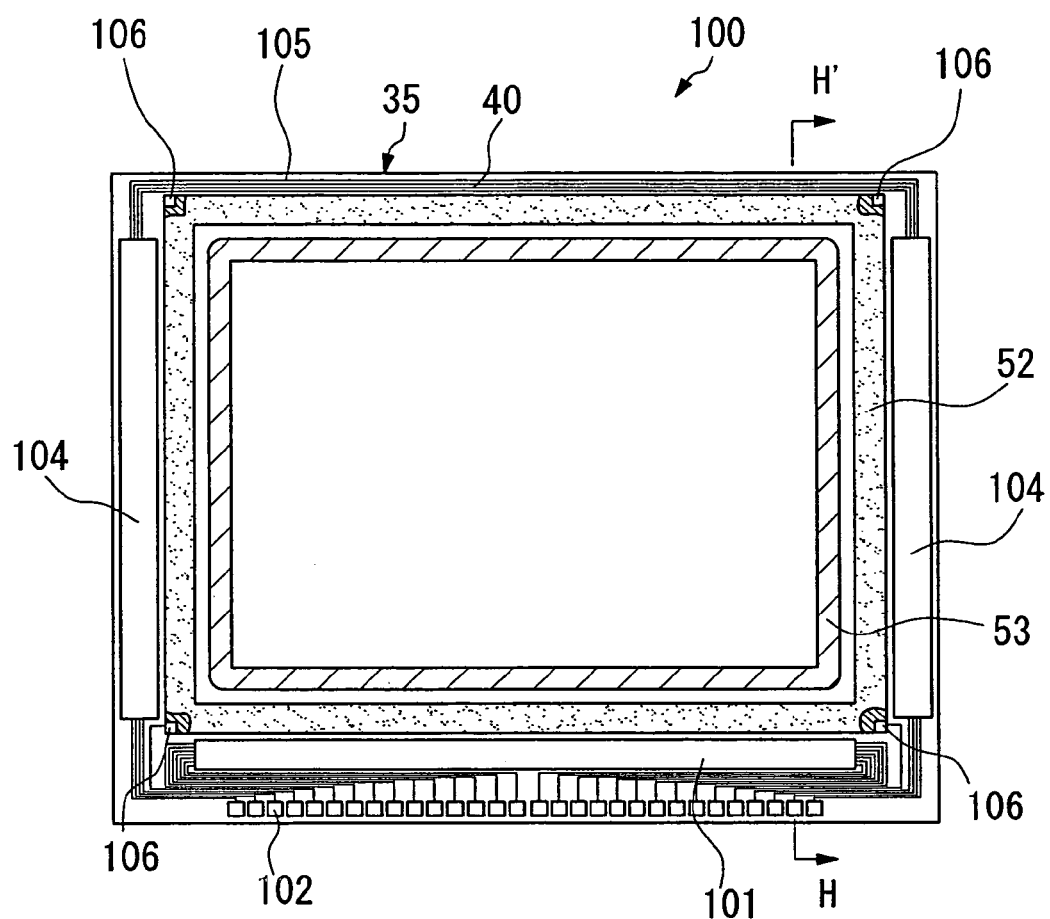
FIG. 5 is a plan view of a liquid crystal display viewed from a counter substrate side.
Figure 6:
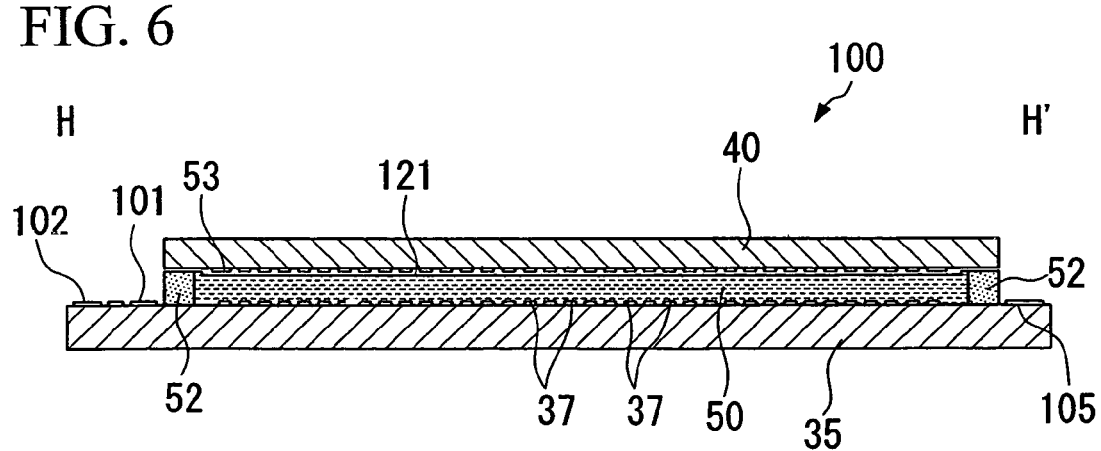
FIG. 6 is a sectional view along line H-H' of FIG. 5.
Figure 7:
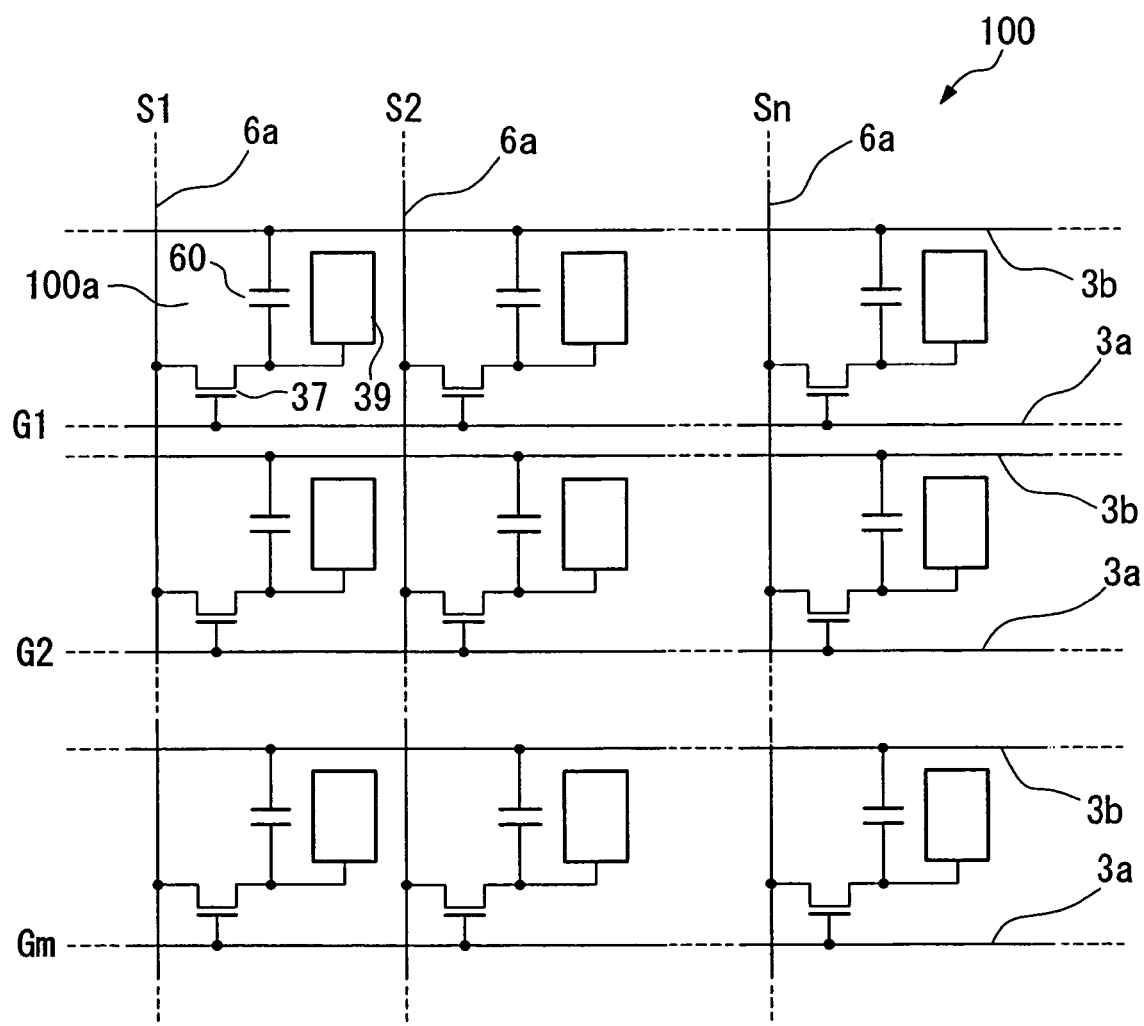
FIG. 7 is an equivalent circuit diagram of the liquid crystal display.
Figure 8:
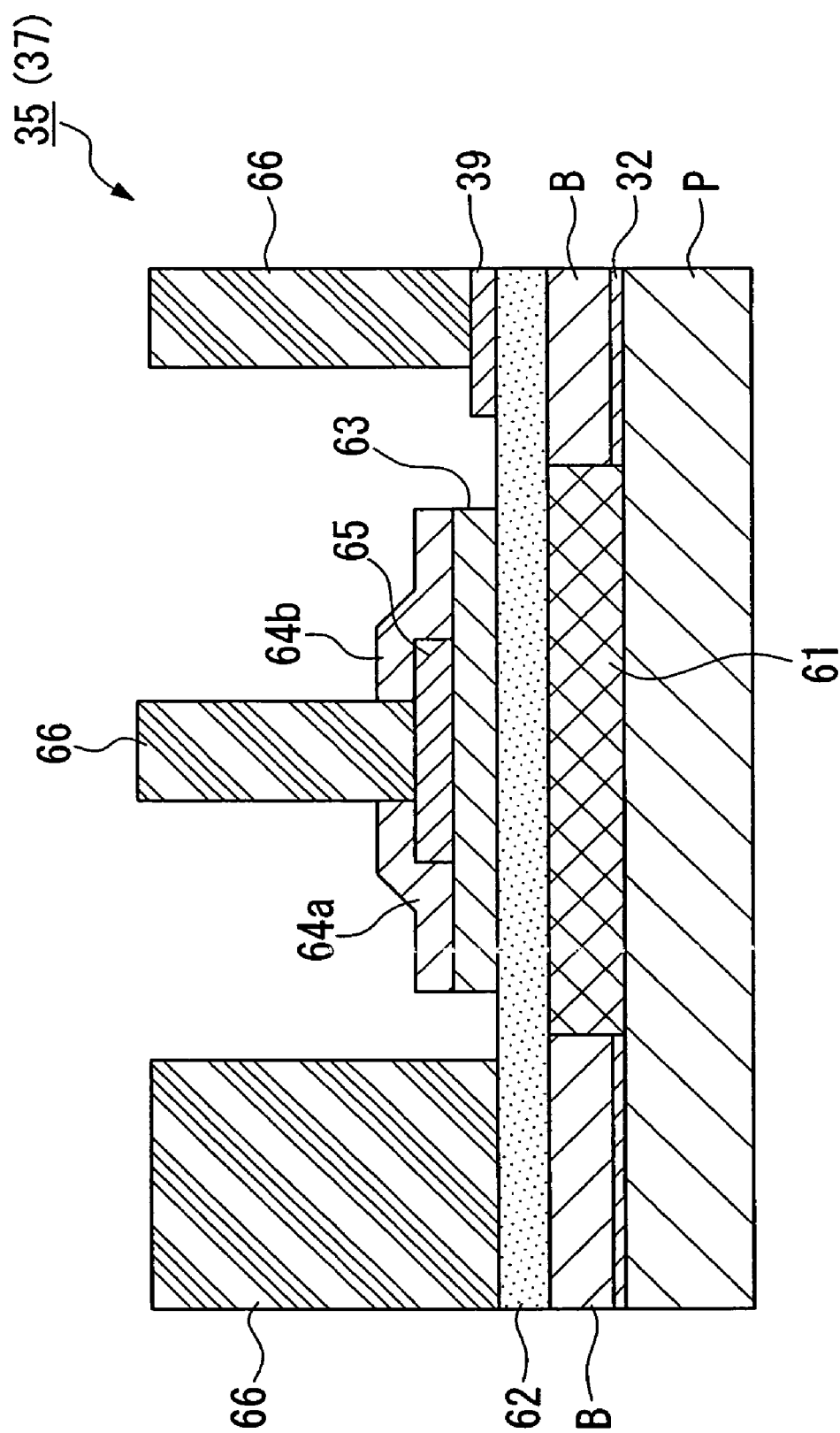
FIG. 8 is an enlarged partial cross-sectional view of the liquid crystal display.

FIG. 5 is a plan view of a liquid crystal display with its system components, viewed from the counter substrate side, and FIG. 6 is a sectional view along line H-H' of FIG. 5. FIG. 7 is an equivalent circuit diagram of a number of elements, their wiring, and the like, in a plurality of pixels formed in a matrix in the image display region of the liquid crystal display. FIG. 8 is an enlarged partial cross-sectional view of the liquid crystal display.

In FIG. 5 and FIG. 6, a liquid crystal display (electro-optical device) 100 of the present embodiment has a TFT array substrate 35 and a counter substrate 40 glued together as a pair by a sealing material 52, being a photocurable sealing material, and liquid crystal 50 is injected into and held in the area enclosed by this sealing material 52. The sealing material 52 forms a closed frame around the area of the substrate surface.

A peripheral partition 53 is formed from a filter material inside the area in which the sealing material 52 is formed. A data line driving circuit 101 and mounting terminals 102 are formed along one side of the TFT array substrate 35, and scan line driving circuits 104 are formed along the two sides adjacent to this side. A plurality of wires 105 is provided along the remaining side of the TFT array substrate 35 to connect between the scan line driving circuits 104 provided on both sides of the image display region. Furthermore, an inter-substrate conducting material 106 is arranged in at least one of the corners of the counter substrate 40 to provide electrical conduction between the TFT array substrate 35 and the counter substrate 40.

Instead of forming the data line driving circuit 101 and the scan line driving circuit 104 on the TFT array substrate 10, a TAB (Tape Automated Bonding) substrate onto which a drive LSI is mounted may be connected electrically and mechanically with a group of terminals formed on the edge of the TFT array substrate 35 via an anisotropic conducting layer, for example. In the liquid crystal display 100, depending on the type of liquid crystal used, that is, the mode of operation such as TN (Twisted Nematic) mode, STN (Super Twisted Nematic) mode, or the like, or normally white mode/normally black mode, a phase contrast plate, a polarizing plate, or the like are arranged at predetermined orientations. However, these are omitted from the figures shown here. Furthermore, in the case where the liquid crystal display 100 is constructed for use in a color display, then red (R), green (G) and blue (B) colored filters, for example, are formed together with protective films in areas on the counter substrate 40 opposite each pixel electrode (described later) on the TFT array substrate 35.

As shown in FIG. 7, in the image display region of the liquid crystal display 100 having such a construction, a plurality of pixels 100a is formed in a matrix, a pixel switching TFT (switching element) 37 is formed for each of the pixels 100a, and data lines 6a, which supply pixel signals S1, S2, to Sn, are connected electrically to the sources of the TFTs 37. The pixel signals S1, S2, to Sn written to the data lines 6a may be supplied sequentially in this order, or may be supplied in a group to a plurality of adjacent data lines 6a. Furthermore, scan lines 3a are connected electrically to the gates of the TFTs 37, and the construction is such that scan signals G1, G2, to Gm are applied sequentially in this order in pulses to the scan lines 3a at predetermined timing.

The pixel electrodes 39 are connected electrically to the drains of the TFTs 37, and write pixel signals S1, S2, to Sn supplied from the data lines 6a are written to the pixels at predetermined timing by turning the TFTs 37, being switching elements, on for a fixed period. The pixel signals S1, S2, to Sn, with predetermined levels, written to the liquid crystal via the pixel electrodes 39 in this manner, are maintained between the pixel electrodes 39 and a counter electrode 121 on the counter substrate 40 as shown in FIG. 6 for a fixed period. In order to prevent the maintained pixel signals S1, S2, to Sn from leaking, storage capacitors 60 are added in parallel with the liquid crystal capacitors formed between the pixel electrodes 39 and the counter electrode 121. For example, the voltage of the pixel electrodes 39 can be maintained by the storage capacitors 60 for three figures of magnitude longer than the time that the source voltage is applied. As a result, the retention characteristics of the electrical charge are improved so that it is possible to realize a liquid crystal display 100 with a high contrast ratio.

FIG. 8 is an enlarged partial cross-sectional view of a liquid crystal display 100 having a bottom gate type TFT 37. A gate wiring 61 formed by a filling method using the above-described filling apparatus 1 is formed between banks B on the glass substrate P forming the TFT array substrate 35.

A semiconductor layer 63 formed from an amorphous silicon (a-Si) layer is laminated onto the gate wiring 61 via a gate insulator 62. The part of the semiconductor layer 63 opposing this gate wire is made to be a channel region. Junction layers 64a and 64b, for obtaining an ohmic contact, and which are formed for example from an n+ type a-Si layer, are laminated onto the semiconductor layer 63, and a insulative etch stop film 65 formed from SiNx for protecting the channel is formed on the semiconductor layer 63 in the central part of the channel region. In addition, the gate insulator 62, the semiconductor layer 63 and the etch stop film 65 are patterned as shown in the figure by the application of a resist coating, then exposed and developed, and photo-etched after vapor deposition (CVD).

Furthermore, the junction layers 64a and 64b, and the pixel electrode 39 formed from ITO, are deposited similarly and photo-etched, and thus patterned as shown in the figure. Then, banks 66 are protruded respectively on the pixel electrode 39, the gate insulator 62 and the etch stop film 65, and by discharging droplets of silver compound between the banks 66 using the above-described droplet discharge apparatus, it is possible to form a source line and a drain line.

In such a liquid crystal display 100, for example when forming the above-described color filter and various wires such as the gate wires 61, and the like, a filling process using the filling apparatus 1 is used.

In this example, the construction is such that the TFTs 37 are used as switching elements for driving the liquid crystal display 100. However, as well as a liquid crystal display, these are also applicable to an organic EL (electroluminescent) device for example, which is described later.

Next is a description of a field emission display (referred to hereunder as FED) incorporating field emission elements as another example of an electro-optical device.

Figure 9B:
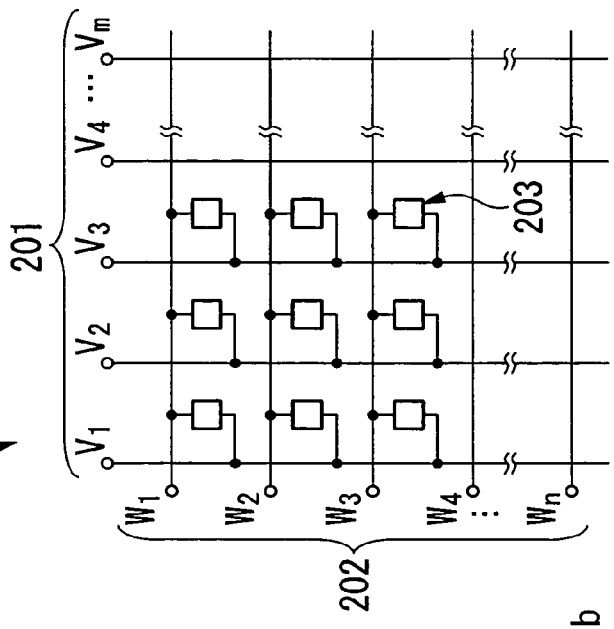
FIG. 9A to FIG. 9C are diagrams showing a field emission display.
Figure 9A:
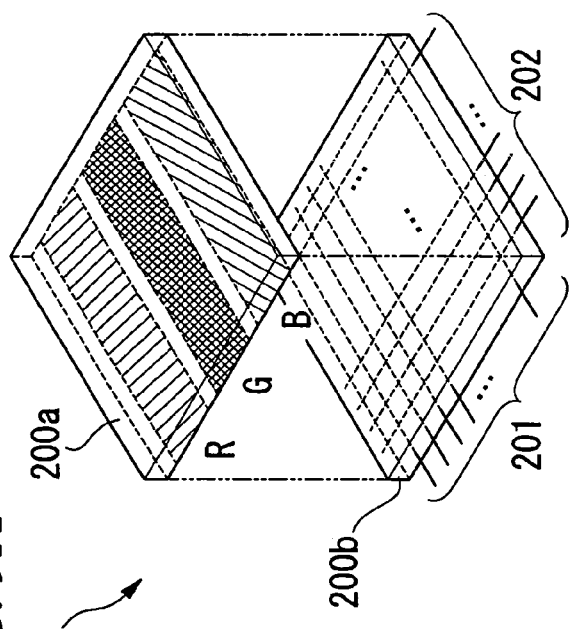
Figure 9C:
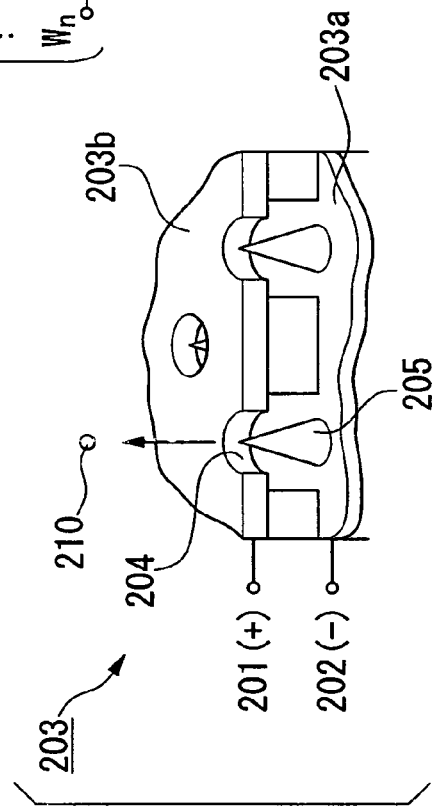

FIG. 9 is a diagram to explain the FED. FIG. 9A is a schematic structural diagram showing the arrangement of a cathode substrate and an anode substrate, which constitute the FED. FIG. 9B is a schematic diagram of a drive circuit in the cathode substrate of the FED, and FIG. 9C is a perspective view showing the main parts of the cathode substrate.

As shown in FIG. 9A, the FED (electro-optical device) 200 has a structure in which a cathode substrate 200a and an anode substrate 200b are placed facing each other. The anode substrate 200b has gate lines 201, emitter lines 202, and field emission elements 203 connected to the gate lines 201 and the emitter lines 202 as shown in FIG. 9B, forming a so-called matrix drive circuit. Gate signals V1, V2, ..., Vm are supplied to the gate lines 201, and emitter signals W1, W2, ..., Wn are supplied to the emitter lines 202. Furthermore, the cathode substrate 200a has RGB fluorescent substances formed on it, and the fluorescent substances have characteristics in that they emit light when struck by electrons.

As shown in FIG. 9C, a field emission element 203 comprises an emitter electrode 203a connected to the emitter line 202, and a gate electrode 203b connected to the gate line 201. Furthermore, the emitter electrode 203a has a protruding section called an emitter tip 205, whose diameter decreases gradually from the emitter electrode 203a side toward the gate electrode 203b side. A hole 204 is formed in a location corresponding to the emitter tip 205 in the gate electrode 203b, and the tip of the emitter tip 205 is positioned in the hole 204.

In such a FED 200, by controlling the gate signals V1, V2, to Vm of the gate lines 201, and the emitter signals W1, W2, to Wn of the emitter lines 202, voltages are applied between the emitter electrodes 203a and the gate electrodes 203b, electrons 210 are emitted from the tips of the emitter tips 205, and the electrons 210 move from the emitter tips 205 towards the holes 204 by electrolytic action. Here, light is emitted when the electrons 210 strike the fluorescent substances on the anode substrate 200b, thus enabling the FED 200 to be driven as desired.

In a FED with such a construction, when forming the emitter electrodes 203a, the emitter lines 202, the gate electrode 203b, the gate lines 201, and the like, for example, a filling process using the filling apparatus 1 is used.

Next is a description of an organic electroluminescence device (referred to hereunder as organic EL device) as another example of an electro-optical device.

FIG. 10 is a sectional side elevation of an organic EL device, denoted by reference number 301. The organic EL device 301 is one where an organic EL element 302 includes a substrate 311, a circuit element section 321, pixel electrodes 331, bank sections 341, light emitting diodes 351, a cathode 361 (counter electrode), and a sealing substrate 371, is connected by the wiring of a flexible substrate (omitted in the figure) to a drive IC (omitted in the figure). The circuit element section 321 is formed on the substrate 311, and a plurality of pixel electrodes 331 is arranged in a line on the circuit element section 321. The bank sections 341 are formed in a grid shape between the pixel electrodes 331, and light emitting diodes 351 are formed in concave apertures 344 formed by the bank sections 341. The cathode 361 is formed over the whole surface of the bank sections 341 and the light emitting diodes 351, and the sealing substrate 371 is laminated onto the cathode 361.

The circuit element section 321 has TFTs 321a with bottom gate type structures. The main structure of each TFT 321a is the same as that shown in FIG. 8. Furthermore, parts of the light emitting diodes 351 are formed using a droplet discharge method.

Such an organic EL device 301 is a so-called high molecular organic EL device having light emitting diodes 351 formed using a droplet discharge method.

The manufacturing process for an organic EL device containing organic EL elements has a bank section forming process for forming bank sections 341, a plasma processing process for enabling appropriate formation of the light emitting diodes 351, a light emitting diode forming process for forming the light emitting diodes 351, a counter electrode forming process for forming the cathode 361, and a sealing process for laminating a sealing substrate 371 onto the cathode 361 for sealing.

The light emitting diode forming process forms the light emitting diodes 351 by forming a hole injection layer 352 and a luminous layer 353 in the concave apertures 344, that is, above the pixel electrodes 331, and comprises a hole injection layer forming process and a luminous layer forming process. The hole injection layer forming process has a first discharge process for discharging a first component (liquid) to form the hole injection layer 352 on the pixel electrodes 331, and a first drying process for drying the discharged first component to form the hole injection layer 352. The luminous layer forming process has a second discharge process for discharging a second component (liquid) to form the luminous layer 353 on the hole injection layer 352, and a second drying process for drying the discharged second component to form the luminous layer 353.

In an organic EL device with such a construction, when forming the hole injection layer and the luminous layer, which constitute the light emitting diode 351, and the gate lines of the TFTs 321*a* with bottom gate type structures, a filling process using the filling apparatus 1 is used.

What is claimed is:

1. A liquid filling method for filling a liquid into a desired location using a discharge head having a cavity for storing a liquid, a nozzle communicated with the cavity, and a discharge device for discharging liquid stored in the cavity through the nozzle, the liquid filling method comprising the steps of:

contacting the nozzle of the discharge head with a liquid prepared in advance, drawing the liquid through the nozzle, and storing the drawn liquid in the cavity; and discharging liquid stored in the cavity using the discharge device, wherein the liquid and the nozzle of the discharge head are contacted by facing the surface in which the nozzle of the discharge head is formed downwardly, and supplying the liquid to the nozzle by a dispenser from below the surface.

* * * * *